(12) United States Patent
Bradley (10) Patent No.: US 6,581,266 B1
(45) Date of Patent: Jun. 24, 2003

(54) METHOD AND APPARATUS FOR PIVOTALLY MOUNTING INSTRUMENTATION ON A LINE

(75) Inventor: William E. Bradley, Westminster, CO (US)

(73) Assignee: University Corporation for Atmospheric Research, Boulder, CO (US)

(*) Notice: Subject to any disclaimer, the term of this patent is extended or adjusted under 35 U.S.C. 154(b) by 106 days.

(21) Appl. No.: 09/702,118

(22) Filed: Oct. 30, 2000

(51) Int. Cl.[7] .............................................. B23P 11/00
(52) U.S. Cl. ....................................... 29/434; 24/136 R
(58) Field of Search ................................. 29/281.5, 282, 29/434; 24/136 R, 115

(56) References Cited

U.S. PATENT DOCUMENTS

| | | | | |
|---|---|---|---|---|
| 904,863 A | * | 11/1908 | Glass ........................ | 24/136 R |
| 2,220,203 A | * | 11/1940 | Branin ....................... | 24/136 R |
| 4,858,810 A | * | 8/1989 | Intlekofer et al. ......... | 24/136 R |
| 5,137,517 A | * | 8/1992 | Loney et al. ............. | 24/115 M |
| 5,224,252 A | * | 7/1993 | Baker et al. ................ | 29/463 |

\* cited by examiner

*Primary Examiner*—Dang Ton
*Assistant Examiner*—Steven Blount
(74) *Attorney, Agent, or Firm*—Duft Setter Ollila & Bornsen LLC (57) ABSTRACT

The instrument package mounting apparatus comprises an axle that serves to eliminate the need to wrap a tether line about the axle. In particular, the axle comprises a cylindrical solid configured with a slot extending from the outer surface of the axle to a substantially central axis thereof, the slot being capable of receiving the tether line. Juxtaposed to this slot and located substantially centered about the substantially central axis of the axle is a rectangular shaped interior channel that functions to receive a pinch bar comprising a substantially rectangular shaped tapered bar. The tapered pinch bar is inserted into the channel formed in the axle and operates to frictionally secure the tether line and the axle. The friction to secure the tether line in the slot, as held in place by the tapered pinch bar is generated by a compression fit formed as the tapered pinch bar is inserted into the interior channel of the axle.

11 Claims, 6 Drawing Sheets

METHOD AND APPARATUS FOR PIVOTALLY MOUNTING INSTRUMENTATION ON A LINE

FIELD OF THE INVENTION

This invention relates to instrumentation packages, and in particular, to an apparatus for pivotally mounting an instrument package to a line, such as a balloon tether line, to enable the instrument package to freely rotate about the line.

PROBLEM

It is a problem in the field of balloon mounted instrument packages to provide an apparatus that enables a user to quickly, simply and reliably attach an instrument package to a balloon tether line in a manner that enables the instrument package to freely rotate about the line. To minimize the size of the balloon required, tether lines are typically constructed from a material with a high strength to weight ratio. However, these tether lines are susceptible to breakage from abrasion, twisting, and kinking stresses. Thus, instrument package attachment systems for tethered balloons must be lightweight, simple to operate, and yet prevent the instrument package from slipping, which causes abrasion of the tether line. The instrument package must also be free to rotate about the tether line with the wind direction to prevent the instrument package from twisting the tether line. Finally, the instrument package attachment system must be constructed with a low profile to reduce wind resistance, which could cause the instrument package to kink the tether line.

There have been a number of past solutions to this problem. The most effective is that disclosed in U.S. Pat. No. 5,410,918, entitled "Ambient Air Sampler." The line attachment apparatus disclosed in U.S. Pat. No. 5,410,918 comprises a stationary axle which is secured to the tether line at respective ends of the axle. End caps fit over the ends of the axle and are received by bearings that are secured to a mounting plate on the air sampler. The bearings allow the air sampler to rotate about the end caps of the axle while the tether line is held stationary within the axle. The mounting plate includes an upper mounting arm fixedly connected to an upper cylindrical bearing and a lower spring-loaded mounting arm connected about a pivot to a lower cylindrical bearing. The spring biases the lower spring-mounted arm into a locked position to hold the axle between the two bearings. The tether line is wound about the axle and secured parallel to the length of the axle by the end caps. A helical groove formed on the outer surface of the axle guides and seats the tether line around the axle when the ends of the axle are inserted into the end caps. A slot or notch formed at each end of the axle receives the line as it exits the groove. The end caps are secured over the two ends of the axle respectively via set screws that frictionally secure the end caps to the axle. Each of the end caps are cylindrically shaped and include a slot formed in the circumference thereof to enable the axle and its attached tether line to be inserted therein and spring loaded into place.

Unfortunately, wrapping large diameter tether lines around the axle is difficult and time consuming. Additionally, the tension generated by a large balloon often prevents the user from gaining sufficient slack in the tether line to enable wrapping about the axle. Furthermore, the use of the end caps to both secure the tether line to the axle and provide the bearing function places a significant amount of stress on the end caps. This results in premature wear or the need to utilize expensive materials in the construction of the end caps.

SOLUTION

The above described problems are solved and a technical advance achieved in the art by the present instrument package mounting apparatus for pivotally mounting an instrument package to a line. The instrument package mounting apparatus comprises an axle, a pinch bar and a pair of bearings. The axle comprises an elongated cylindrical body having an interior channel configured to receive the tether line and the pinch bar. The pinch bar is tapered and configured to insert into the channel with the tether line to frictionally secure the axle to the tether line using a compression connection created by the taper of the pinch bar as the pinch bar is inserted. A slot juxtaposed to the interior channel and extending substantially the length of the axle provides access to the interior channel for receiving the tether line. At least one end of the axle includes an aperture for insertion of the pinch bar into the channel to frictionally secure the axle to the tether line. The bearings terminate the ends of the axle to provide a rotational attachment to an instrument package. In particular a first one of the bearings is connected to a first end of the axle and a second one of the bearings is connected to a second end of the axle to provide the rotational attachment to the instrument package. The bearings permit the instrument package to freely rotate about the axle, which internally secures the tether line via that friction force generated by the tapered pinch bar.

In some examples of the present instrument mounting apparatus, the axle comprises a two piece axle design, wherein a first and a second segment of the axle each comprise mating segments of a cylindrical solid that define the interior channel and the slot juxtaposed to the channel. A plurality of fasteners secure the first and second axle pieces together. In addition, the respective bearing connected to each end of the axle provides further reinforcement of the connection between the first and second axle pieces.

In other examples of the present instrument package mounting apparatus, the axle comprises a three piece axle design. In particular a first segment, a second segment, and a third segment each comprise mating segments of the cylindrical solid that define the interior channel and the slot juxtaposed to the channel. The first segment, the second segment, and the third segment are assembled by fasteners, which are tightened to secure the second segment and third segment to the first segment. As with the prior example, the respective bearing connected to each end of the axle provides further reinforcement of the connection between the first, second, and third axle pieces.

A first advantage of the present instrument package mounting apparatus is that the slot and channel can be configured in a plurality of dimensions to accommodate various tether line sizes. A second advantage of the present instrument package mounting apparatus is that it receives the tether line internal to the axle. This eliminates the prior art requirements of generating enough slack in the tether line to wrap the tether line about the axle and align the tether line with the helical grooves at each end of the axle. A third advantage of the present instrument package mounting apparatus is that the axle and the pinch bar provide the attachment to the tether line thereby eliminating the need for the end caps of the prior art. A fourth advantage of the present instrument package mounting apparatus is that the tether line is frictionally secured to the axle in a substantially uniform manner along the length of the axle to eliminate stress points. A fifth advantage of the present instrument package mounting apparatus is that grooves in the channel could be used to accommodate various sizes of tether line without reconfiguration of the axle.

DETAILED DESCRIPTION

It is common practice to attach instrument packages to a balloon tether line to enable the balloon to transport instrument packages to a location where measurements are to be taken by the instrument packages. For example, air sampling systems are used in many applications to measure trace gases for atmospheric research. For low altitude air sampling, tethered balloons are typically used to perform air sample measurements up to 1,000 meters above the ground. The balloon is attached to a tether line that is controllably released by a winch. One or more instrument packages are attached to the tether line to perform the desired measurements. The typical tether line is made from a material that has a high strength to weight ratio to minimize the size of the balloon required. However, these tether lines are susceptible to breakage from abrasion, twisting and kinking stresses. Thus, the instrument package attachment system for tethered balloons must be lightweight, simple to operate, and yet not allow the instrument package to slip and cause abrasion of the tether line. The instrument package must also be free to rotate about the tether line with the wind direction to prevent the instrument package from twisting the tether line. Finally, the instrument package attachment system must include a low profile to reduce wind resistance, which could cause the instrument package to kink the tether line.

Figure 1:
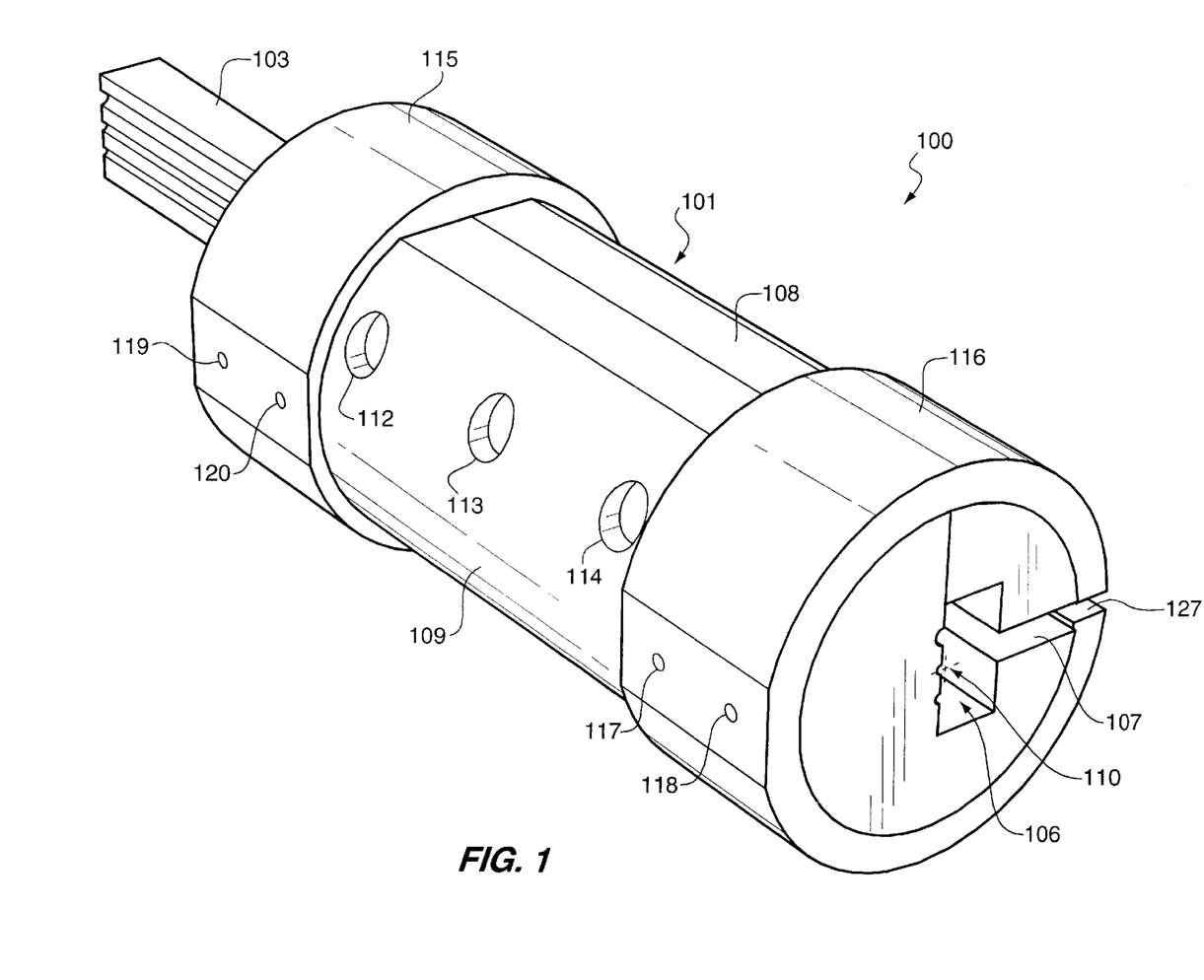
FIG. 1 illustrates a perspective view of an example of the present instrument package mounting apparatus.
Figure 2:
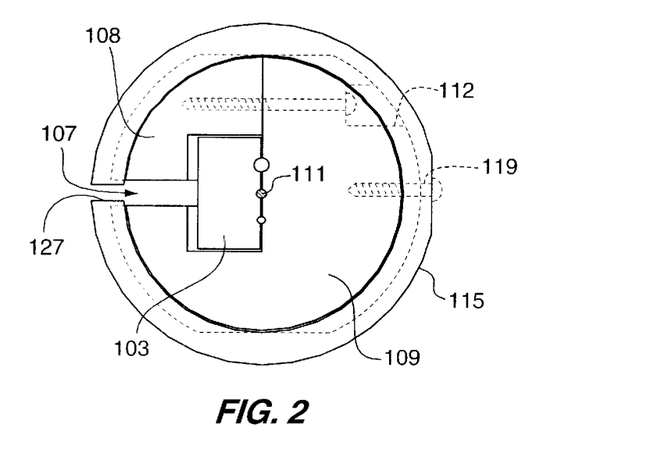
FIG. 2 illustrates a cross-sectional view of the instrument package mounting apparatus of FIG. 1.
Figure 3:
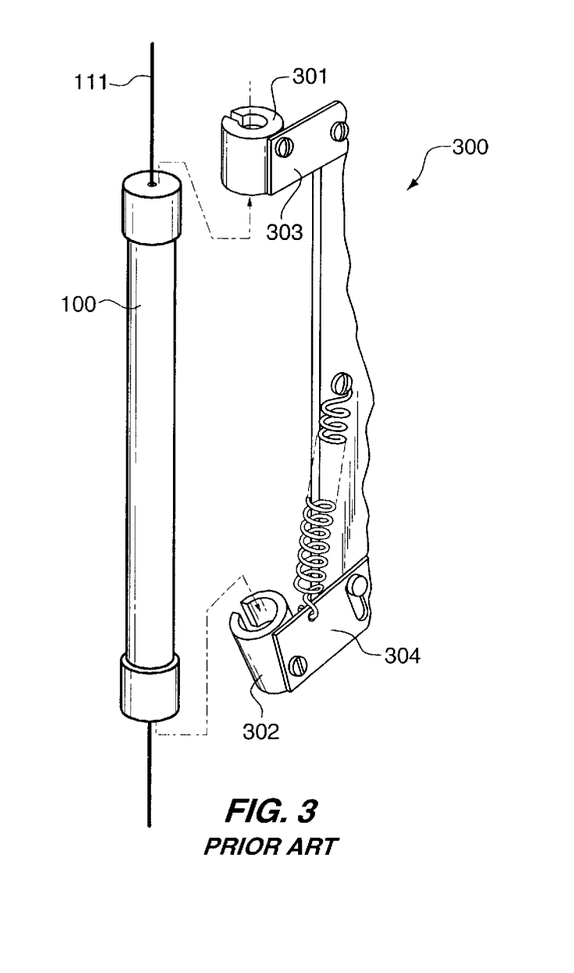
FIG. 3 illustrates a prior art instrument package mounting mechanism.

Referring to FIGS. 1–3, the instrument package mounting apparatus 100 comprises an axle 101 a pinch bar 103, a first bearing 115 and a second bearing 116. The axle 101 comprises an elongated cylindrical body having defined therein an interior channel 106 and slot 107 juxtaposed to the channel 106. In some examples of the present instrument package mounting apparatus 100, the axle 101 could be constructed from a single piece of stock configured with the channel 106 and the slot 107. In other examples of the present instrument package mounting apparatus 100, the axle 101 could comprise a first segment 108 and a second segment 109 that comprise mating segments of a cylindrical solid to form the axle 101. The portion of the cylindrical solid that each of the first 101 and second 102 axle segments implement result in the slot 107 that extends along the length of the axle 100 from the outer surface of the axle 100 to a substantially central axis 110. The slot 107 is configured to receive a tether line 111, illustrated in FIG. 2, internal to the axle 101. Juxtaposed to the slot 107 and located substantially centered about the axis 110 of the axle 101 is the rectangular shaped interior channel 106 that functions to receive the pinch bar 103. The pinch bar 103 comprises a substantially rectangular shaped solid that is tapered along its length so that it forms a compression fit with the interior channel 106 when the pinch bar 103 is inserted into the channel 106. Operationally, the pinch bar 103 is inserted into the channel 106 and serves to secure the tether line 111 via frictional force created by the compression fit. Fasteners 112–114 provide the connection between the first segment 108 and the second segment 109. Advantageously, the two piece axle design comprising the first segment 108 and the second segment 109 significantly reduces the manufacturing technology required to produce the axle 101.

The ends of the assembled first segment 108 and the second segment 109 of the axle 101 are terminated by respective bearings 115 and 116. The bearings 115 and 116 include a slot, e.g. 127, that aligns with the slot 107, formed by the first segment 108 and the second segment 109. The slots, e.g. 127 in the bearings 115 and 116 in combination with the slot 107 permit the tether line 111 to be received in the channel 106 during attachment of the instrument package mounting apparatus 100 to the tether line 111. Fasteners 117–120 provide the connection between the bearings 115 and 116 and the axle 101. The bearings 115 and 116 provide a rotational attachment to the instrument package mounting mechanism 300, illustrated in FIG. 3. In particular the bearings 115 and 116 insert into the first and second axle mounts 301 and 302 and freely rotate therein. It should be noted that the instrument package mounting mechanism 300 connects to the mounting plate on an instrument package in a conventional manner with the upper mounting arm 303 fixedly connected and the lower spring-loaded mounting arm 304 pivotally connected to the mounting plate. Thus, the first and second bearings, 115 and 116, in combination with the axle mounts 301 and 302 form a rotatable bearing mechanism to enable the instrument package to freely rotate about the axle 101. The axle 101 in turn securely holds the tether line 111 via the friction force generated by the tapered pinch bar 103 inserted into the channel 106.

Figure 4:
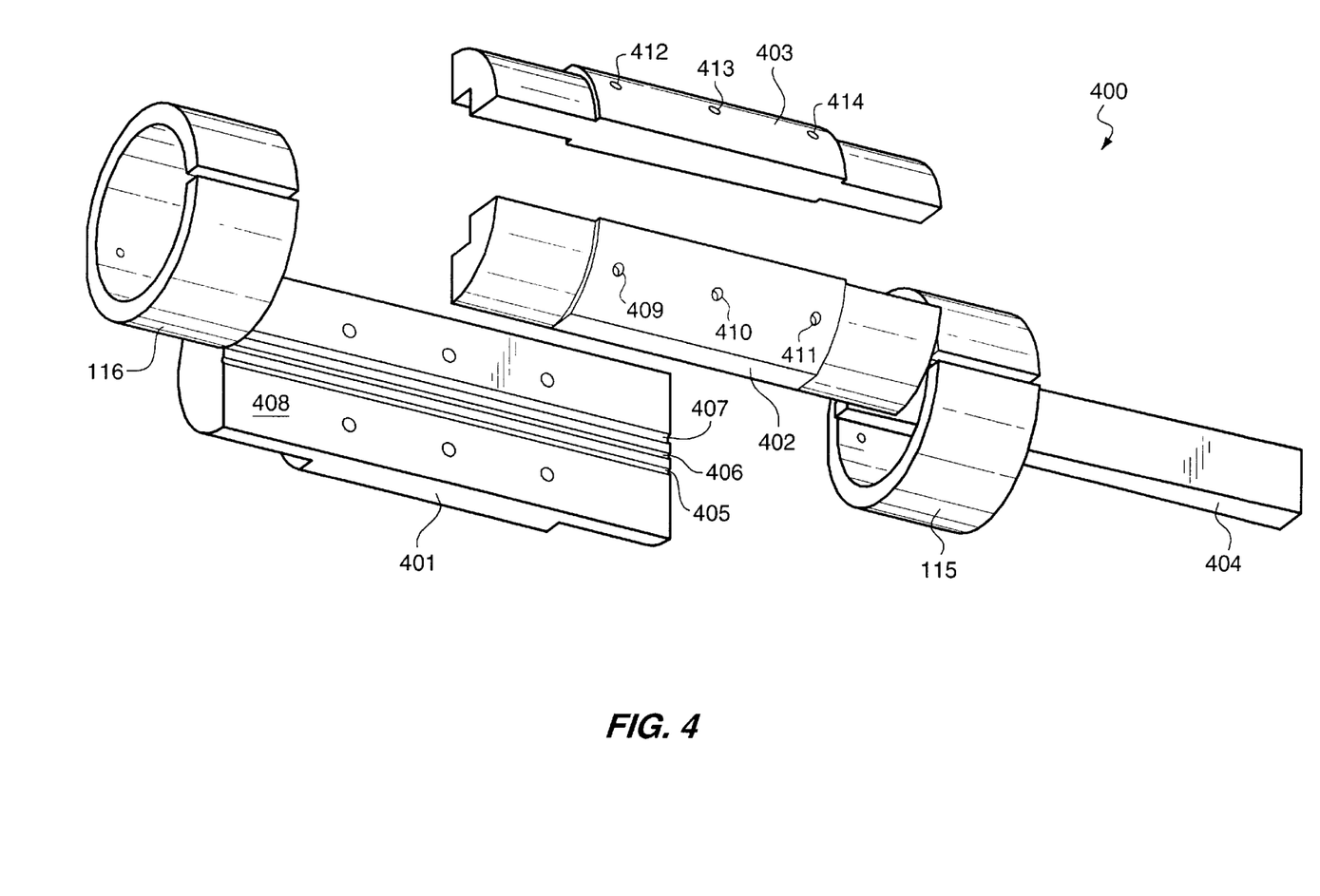
FIG. 4 is an exploded top perspective view of another example of the present instrument package mounting apparatus.
Figure 5:
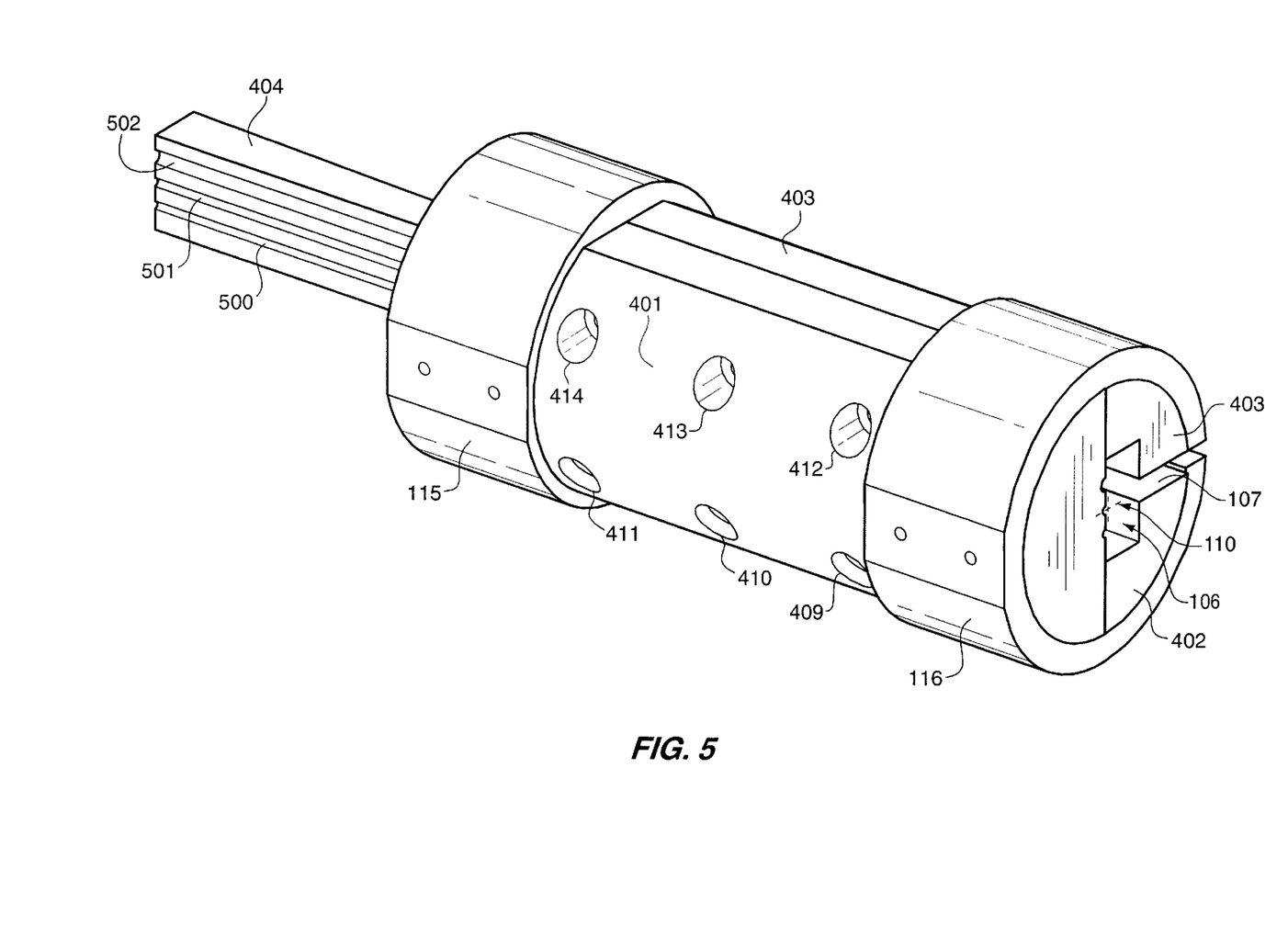
FIG. 5 illustrates a perspective view of the instrument package mounting apparatus of FIG. 4.

FIGS. 4 and 5 illustrate another example of an instrument package mounting apparatus 400 according to the present invention. It is anticipated however, that one skilled in the art will recognize numerous other examples in accordance with the principles described below, and thus, the following examples are for the purpose of illustration and not limitation. Those skilled in the art will also appreciate that various features described below could be combined with the above described embodiment to form multiple variations of the invention.

The instrument package mounting apparatus 400 comprises a three piece axle 400, the first bearing 115, the second bearing 116 and the tapered pinch bar 404. As with the axle 100, the bearings 115 and 116 of axle 400 provide the rotational attachment to the mounting mechanism 300. The axle 400 comprises a first segment 401, a second segment 402, and a third segment 403 that form mating segments of the cylindrical solid that comprises axle 400. The portion of the cylindrical solid that each of the first 401, the second 402, and third 403 axle segments implement results in slot 107 that extends from the outer surface of the axle 400 to a substantially central axis 110. As with axle 100, the slot 107 is configured to receive the tether line 111 internal to the axle 400. Juxtaposed to the slot 107 and located substantially centered about the axis 110 of the axle 400 is the rectangular shaped channel 106 that functions to receive the tapered pinch bar 404 and the tether line 111. A plurality of fasteners, 409–414, secure the second 402 and the third 403 segments to the first segment 401 to form the axle 400.

The first segment 401 of the axle 400 includes a plurality of grooves 405–407 formed in the planer surface 408. The individual grooves 405, 406, and 407 are each individually configured to receive a different size of tether line, e.g. 111. Advantageously, this permits the instrument package mounting apparatus 400 to accommodate various tether line sizes that could be used to launch various balloon sizes. The grooves 405–407 mate with corresponding grooves 500–502 formed in the tapered pinch bar 404 to form individual cavities within the interior channel 106 that are slightly smaller than the tether line size the cavities are configured to accommodate. Operationally, the tether line 111 is received into the interior channel 106 via the slot 107 and aligned with the one of the grooves 405–407 dimensioned for the tether line 111. The tapered pinch bar 404 is also inserted into the channel 106 with the mating groove e.g. 502 forming the cavity around the tether line 111. Advantageously, the cavities engage the tether line 111 in a substantially uniform manner to eliminate stress points that could damage the tether line 111.

Figure 6:
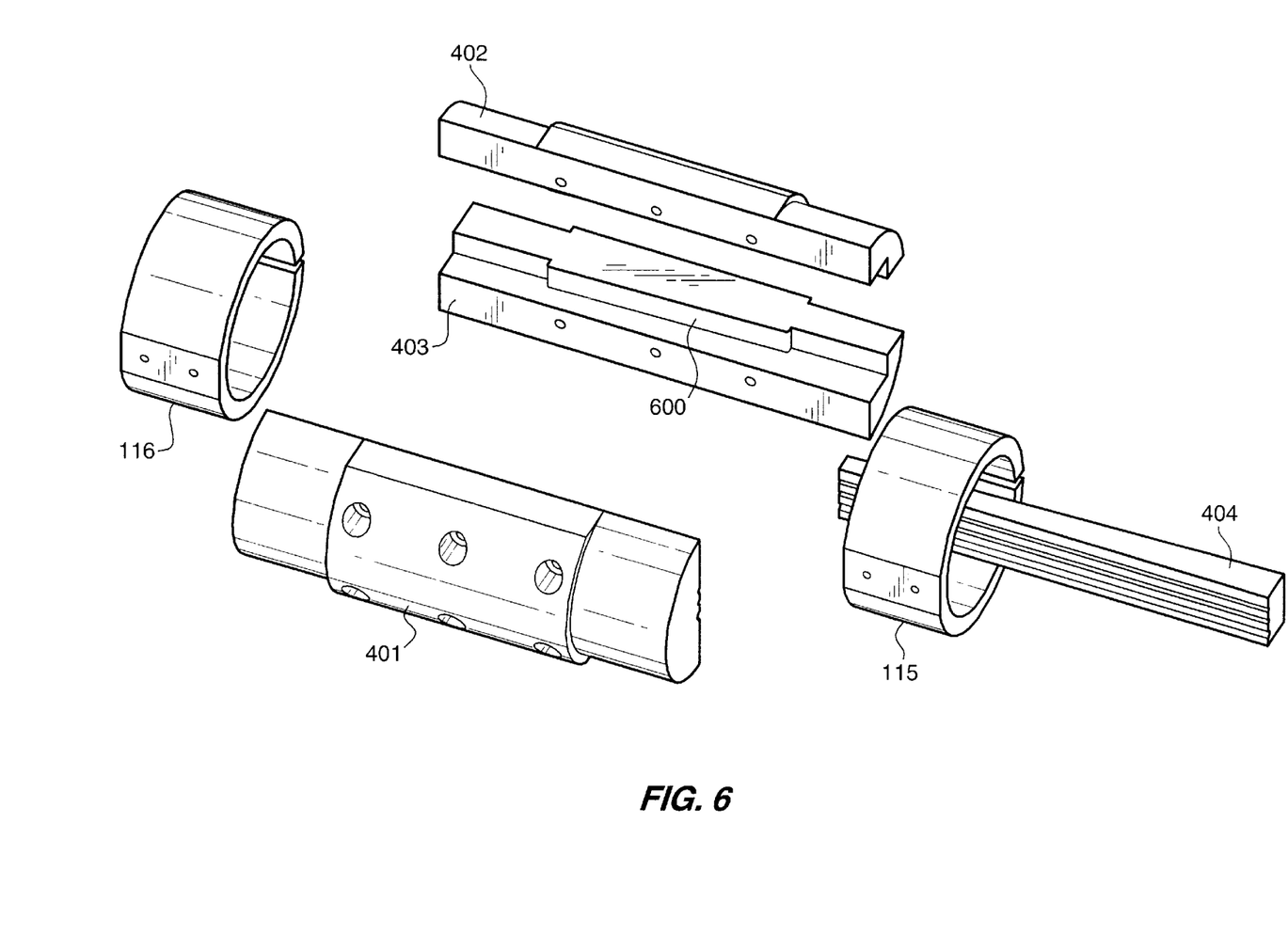
FIG. 6 illustrates an exploded side perspective view of the present-instrument package mounting apparatus.

Referring to FIG. 6, the friction to secure the axle 400 to the tether line 111 is provided by the taper of the pinch bar 404. The first segment 402 and the second segment 403 include a sloped ramp 600 in the portion of the first segment 402 and the second segment 403 that forms the interior channel 106. The slope of the ramp 600 corresponds to the taper of the pinch bar 404 so that when the pinch bar 404 is inserted into the channel 106 the tapered pinch bar 404 and sloped ramp 600 form a compression fit to apply the necessary frictional force that secures the axle 400 to the tether line 111.

Figure 7:
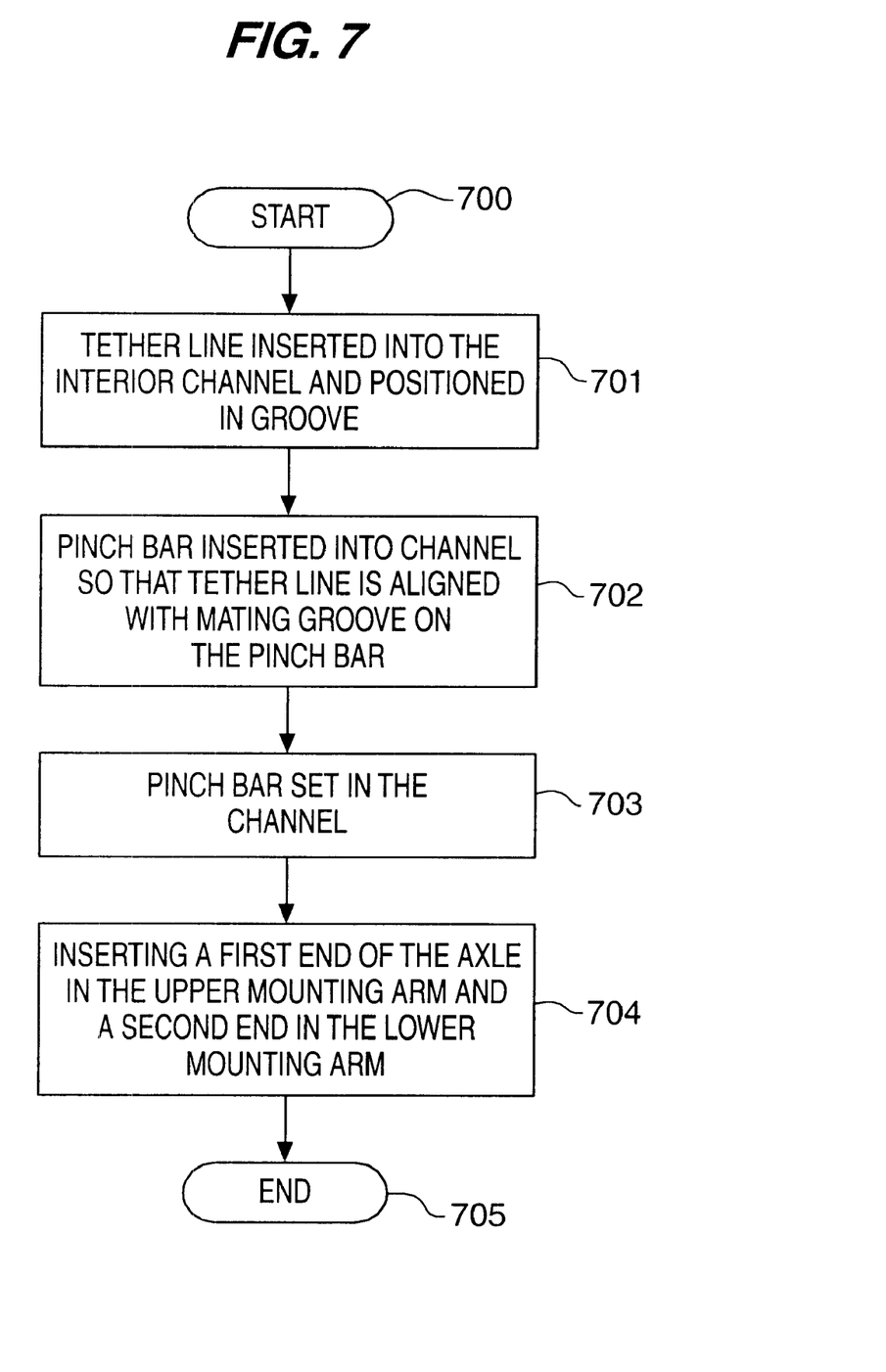
FIG. 7 is a flow chart illustrating the operation of an instrument package mounting apparatus according to the present invention.

FIG. 7 is a flow chart illustrating the operation of the instrument package mounting apparatus 400 according to the present invention. Those skilled in the art will appreciate that the operation of the instrument package mounting apparatus 100 would be similar. On FIG. 7 the operation begins at step 700. At step 701, the tether line 111 is inserted into the interior channel 106 of the axle 400 and positioned so that the tether line is in a corresponding one of the grooves 405–407. At step 702 the pinch bar is inserted into the channel 106 so that the tether line 111 is aligned with the mating one of the grooves 500–501 on the pinch bar 404. During the insertion of the pinch bar 404 into the channel 106 the pinch bar 404 engages the interior ramp 600 to form the compression fit between the pinch bar 404 and the interior channel 106. At step 703, the pinch bar is set in the channel 106. Setting the pinch bar 404 is representative of compressing the pinch bar into the channel 106 toward the end of the insertion to firmly seat the pinch bar in the channel and create the compression fit and friction required to secure the tether line 111 in the axle 400. Setting the pinch bar 404 could be accomplished by any appropriate method. Some examples include without limitation, smacking the extended end of the pinch bar 404 smartly with the palm of your hand, or using a mallet or other similar device to set the pinch bar in the channel 106. At step 704 a first end of the axle 400 is inserted into the upper mounting arm 303 that is fixedly connected and the second end of the axle 400 is inserted into the lower spring-loaded mounting arm 304 to mount the instrument package on the tether line 111. The method ends at step 705.

Those skilled in the art will appreciate variations of the above-described embodiments that fall within the scope of the invention. As a result, the invention is not limited to the specific examples and illustrations discussed above, but only by the following claims and their equivalents.

What is claimed:

1. Apparatus for attaching an instrument package to a tether line comprising:

first and second attachment means fixedly connected to the instrument package;

axle means having a first end and a second end, wherein the first end is insertable into the first attachment means and the second end is insertable into the second attachment means so that the axle means is rotatable in the first and second attachment means, the axle means comprising:

an elongated cylindrical body, wherein the body defines an interior channel for receiving the tether line internal to the body and wherein the tether line is admitted into the interior channel by a first slot juxtaposed to the channel, with the first slot extending uninterruptedly from an outer surface of the axle to the interior channel and extending substantially the length of the body; and a pinch bar insertable in the channel and configured to frictionally engage the tether line in the channel when the tether line is inserted into the channel;

wherein in use the tether line is inserted into the interior channel of the axle and the pinch bar is inserted into the interior channel and frictionally engages the tether line in the interior channel.

2. The apparatus of claim 1 wherein the axle means further comprises:

a first segment that forms a first half of the elongated cylindrical body; and a second segment that forms a second half of the elongated cylindrical body, wherein the first segment and the second segment are interconnected by a plurality of fasteners to form the elongated cylindrical body.

3. The apparatus of claim 2 wherein one of the first segment and the second segment further comprises:

at least one interior groove extending substantially the length of the one of the first segment and the second segment and configured to position the tether line in the channel.

4. The apparatus of claim 2 wherein one of the first segment and the second segment further comprises:

a plurality of interior grooves extending substantially the length of the one of the first segment and the second segment, wherein each individual one of the plurality of interior grooves is configured to receive a different sized tether line and to position the received tether line in the channel.

5. The apparatus of claim 1 wherein the axle means further comprises:

a first segment that forms a first half of the elongated cylindrical body;

a second segment that forms a first third of the elongated cylindrical body; and a third segment that forms a second third of the elongated cylindrical body, wherein the second segment and the third segment are interconnected by a plurality of fasteners to the first segment to form the elongated cylindrical body.

6. The apparatus of claim 5 wherein the first segment further comprises:

at least one interior groove extending substantially the length of the first segment configured to position the tether line in the channel.

7. The apparatus of claim 5 wherein the first segment further comprises:

a plurality of interior grooves extending substantially the length of the first segment, wherein each individual one of the plurality of interior grooves is configured to receive a different sized tether line and position the received tether line in the channel.

8. The apparatus of claim 1 further comprising:
- a first bearing fixably connected to the first end of the elongated cylindrical body and configured with a second slot that mates with the first slot juxtaposed to the channel in the elongated cylindrical body for receiving the tether line; and
- a second bearing fixably connected to the second end of the elongated cylindrical body and configured with a third slot that mates with the first slot juxtaposed to the channel in the elongated cylindrical body for receiving the tether line.

9. The apparatus of claim 1 wherein the pinch bar comprises:
- a substantially rectangular shaped bar that is tapered along its length from a first end thereof to a second end thereof so that the pinch bar frictionally engages the tether line in a compression fit as a wider portion of the taper inserts into the channel.

10. A method for attaching an instrument package to a tether line, the method comprising:
- inserting a tether line into an interior channel of an axle via a slot defined in the axle, with the slot extending uninterruptedly from an outer surface of the axle to the interior channel;
- inserting a pinch bar into the interior channel to frictionally secure the axle and the tether line; and
- connecting the axle to an instrument package.

11. The method of claim 10 wherein the step of inserting the tether line further comprises:
- positioning the tether line in a groove defined in the interior channel, wherein the groove mates with a corresponding groove in the pinch bar to form a cavity for the tether line when the pinch bar is inserted into the interior channel.

* * * * *